US009467769B2

(12) United States Patent
Liu et al.

(10) Patent No.: US 9,467,769 B2
(45) Date of Patent: Oct. 11, 2016

(54) HEADSET COMMUNICATION METHOD UNDER A STRONG-NOISE ENVIRONMENT AND HEADSET

(71) Applicant: Goertek, Inc., Weifang, ShanDong Province (CN)

(72) Inventors: Song Liu, Weifang (CN); Jian Zhao, Weifang (CN)

(73) Assignee: GOERTEK, INC., Weifang, Shandong Province (CN)

( * ) Notice: Subject to any disclaimer, the term of this patent is extended or adjusted under 35 U.S.C. 154(b) by 105 days.

(21) Appl. No.: 14/385,075

(22) PCT Filed: May 22, 2014

(86) PCT No.: PCT/CN2014/078081
§ 371 (c)(1),
(2) Date: Sep. 12, 2014

(87) PCT Pub. No.: WO2014/187332
PCT Pub. Date: Nov. 27, 2014

(65) Prior Publication Data
US 2016/0241948 A1 Aug. 18, 2016

(30) Foreign Application Priority Data
May 22, 2013 (CN) .......................... 2013 1 0192821

(51) Int. Cl.
*H04B 15/00* (2006.01)
*H04R 1/10* (2006.01)
*G10L 21/0272* (2013.01)
*G10L 21/0364* (2013.01)

(52) U.S. Cl.
CPC ......... *H04R 1/1083* (2013.01); *G10L 21/0272* (2013.01); *G10L 21/0364* (2013.01); *H04R 2410/01* (2013.01); *H04R 2460/01* (2013.01)

(58) Field of Classification Search
CPC ............ H04R 1/1083; H04R 2410/01; H04R 2460/01; G10L 21/0272; G10L 21/0364
USPC ....................................... 381/94.2
See application file for complete search history.

(56) References Cited

U.S. PATENT DOCUMENTS

2009/0010442 A1* 1/2009 Usher ...................... H03G 3/32
381/57

FOREIGN PATENT DOCUMENTS

CN 102300140 A 12/2011

OTHER PUBLICATIONS

PCT/CN2014/078081, PCT Written Opinion of the International Searching Authority, dated Aug. 20, 2014, both Chinese version and English translation, 9 pages.

*Primary Examiner* — Paul S Kim
(74) *Attorney, Agent, or Firm* — Boyle Fredrickson, S.C.

(57) ABSTRACT

The invention discloses a headset communication method under a strong-noise environment and a headset. The method comprises: using earplugs to reduce medium and high frequency noises entering an ear canal, using an external connection cavity in parallel connection with the ear canal to divert medium and low frequency noises; using an internal microphone to pick up the sound in the ear canal and an environmental noise signal entering the ear canal, using an external microphone to pick up the environmental noise signal, and taking the external microphone signal as reference signals to eliminate the noise element in the internal microphone signal and remain the voice element to obtain transmitting terminal signals of the headset; using sound dynamic compression technology to cut down and compensate the signals picked up by the external microphone in terms of sound pressure level such that the sound pressure range is compressed to a range acceptable by human ears and the signals picked up by the external microphone and the receiving terminal signal received by the headset are broadcast together through a receiver of the headset. By means of the technical scheme of the present invention, the functions of protecting hearing, enhancing voice and monitoring a three-dimensional environment can be achieved comprehensively under strong-noise environments.

10 Claims, 5 Drawing Sheets

HEADSET COMMUNICATION METHOD UNDER A STRONG-NOISE ENVIRONMENT AND HEADSET

TECHNICAL FIELD

The invention relates to the field of acoustics technology, particularly to a headset communication method under a strong-noise environment and headset.

BACKGROUND ART

With social progress and economic development, everywhere we can see the situation where human beings have to face strong noise environment, e.g., when operating next to a large machine (such as loom lathes, air compressors, blowers, etc.) in the industrial production, presenting in roar of modern transports (such as motorcycles, trains, airplanes, etc.), and being in construction sites or military battlefields, and so on. Strong noise can cause a number of serious problems.

Firstly, the high-intensity noise may make people feel tired and produce negative emotions and seriously damage people's nervous system, blood circulatory system, endocrine system and digestive system as well as vision, hearing and intelligence. Therefore, hearing protection in a strong noise environment is an essential measurement. Secondly, in a strong noise environment, the speaker's voice signals may be completely submerged by ambient noises when using a headset for voice communication, so voice communication process cannot be properly achieved, which may lead to serious impact on production, life, military operations, etc and huge losses to individuals, organizations and even a country. As can be seen, it is significantly important to maintain a clear and stable voice communication function, which has also been a hot topic for researchers. Thirdly, in some strong noise environments, while people's hearing is protected, they also need to keep sensitive to the sound in the surrounding environment enough to monitor real time changes in the surrounding environment so as to make correct response, otherwise they may be unconscious of possible danger signals. For example, in a battlefield environment, the soldiers would apparently be in a very passive and dangerous situation if they cannot hear the ambient sound.

SUMMARY OF THE INVENTION

Accordingly, the present invention provides a headset and a headset communication method under a strong-noise environment that can ensure the headset communication quality, to overcome or at least partially solve the above problem.

To achieve the above object, the technical solution of the present invention is achieved as follows:

The present invention discloses a headset communication method under a strong-noise environment, the method comprising:

using an earplug closely coupled to the wearer's ear canal meatus to reduce medium and high frequency noises entering the ear canal, and using an external connection cavity extending from the earplug and constituting a parallel branch with the ear canal to divert medium and low frequency noises entering the ear canal, so as to reduce noises from the sound signals entering the ear canal in a full frequency range;

using an internal microphone of the headset to pick up voice signals within the ear canal and environmental noise signals slipping into the ear canal, and using an external microphone of the headset to pick up environmental noise signals and voice signals propagating through air; and obtaining transmitting terminal signals of the headset after eliminating the noise element in the signals picked up by the internal microphone and remaining the voice element with the signals picked up by the external microphone as reference signals;

cutting down and compensating the signals picked up by the external microphones at both sides of the headset in terms of sound pressure level such that the sound pressure range of the processed signals is compressed to a range acceptable by human ears and the processed signals and the receiving terminal signals received by the headset are broadcast together through a receiver of the headset.

Alternatively, the acoustic impedance of the external connection cavity is significantly smaller than the acoustic impedance of the ear canal; and a sound absorbing material is attached to the inner wall of the external connection cavity.

Alternatively, the step of obtaining transmitting terminal signals of the headset after eliminating the noise element in the signals picked up by the internal microphone and remaining the voice element with the signals picked up by the external microphone as reference signals, comprises:

determining a control parameter $\alpha$ according to the statistical energy ratio of the signals picked up by the external microphone to the signals picked up by the internal microphone in a low frequency range; and updating the weight of the self-adaptive filter with the feedback output signals, controlling the updating speed of the weight of the self-adaptive filter with the control parameter $\alpha$, and self-adaptively filtering the signals picked up by the external microphone, to obtain self-adaptive filter output signals;

obtaining output signals by subtracting the self-adaptive filter output signals from the signals picked up by the internal microphone; and using the output signals as transmitting terminal signals of the headset.

Optionally, the method further comprises: single-channel voice processing and spectrum spreading processing the output signals; and using the single-channel voice processed and spectrum spreading processed signals as transmitting terminal signals of the headset.

The present invention also discloses a headset, the headset comprising:

an earplug closely coupled to the wearer's ear canal meatus to reduce medium and high frequency noises entering the ear canal; an external connection cavity extending from the earplug and constituting a parallel branch with the ear canal to divert medium and low frequency noises entering the ear canal;

an internal microphone for picking up voice signals within the ear canal and environmental noise signals slipping into the ear canal; an external microphone for picking up environmental noise signals and voice signals propagating through air; a voice signal processing unit for receiving the signals picked up by the internal microphone and the signals picked up by the external microphone and obtaining transmitting terminal signals of the headset after eliminating the noise element in the signals picked up by the internal microphone and remaining the voice element with the signals picked up by the external microphone as reference signals;

a sound dynamic compression unit for using sound dynamic compression technology to cut down and compensate the signals picked up by the external microphone in terms of sound pressure level such that the sound pressure range of the processed signals is compressed to a range acceptable by human ears; and a receiver for broadcasting the signals processed by the sound dynamic compression unit and the receiving terminal signals received by the headset together.

Alternatively, the acoustic impedance of the external connection cavity is significantly smaller than the acoustic impedance of the ear canal; and a sound absorbing material is attached to the inner wall of the external connection cavity.

Alternatively, the voice signal processing unit comprises:

a voice detection module for receiving the signals picked up by the internal microphone and the signals picked up by the external microphone, determining a control parameter $\alpha$ according to the statistical energy ratio of the signals picked up by the external microphone to the signals picked up by the internal microphone in a low frequency range, and outputting the control parameter $\alpha$;

a self-adaptive filter for updating the reference signals with the feedback output signals as the weight, updating the control parameter of the speed with the control parameter $\alpha$ as the weight, self-adaptively filtering the signals picked up by the external microphone, and outputting the self-adaptive filter output signals;

and, a noise reduction module for obtaining output signals by subtracting the received self-adaptive filter output signals from the received signals picked up by the internal microphone.

Alternatively, the voice processing unit further comprises:

a post-processing module for single-channel voice processing and spectrum spreading processing the output signals.

Alternatively, the voice signal processing unit and the sound dynamic compression unit are integrated into a DSP chip.

Alternatively, the number of the internal microphone is 1, which is located on the left or right ear side of the headset; the number of the external microphone is 2, which are located on the left and right ear sides of the headset, respectively;

the voice signal processing unit receives the signals picked up by the internal microphone and the external microphone that are located at the same ear side; and the sound dynamic compression unit cuts down and compensates the signals picked up by the two external microphones in terms of sound pressure level.

By means of the technical solution of using an earplug closely coupled to the wearer's ear canal meatus to reduce medium and high frequency noises entering the ear canal, and using an external connection cavity extending from the earplug and constituting a parallel branch with the ear canal to divert medium and low frequency noises entering the ear canal, the noises can be reduced from the voice signals entering the ear canal in a full frequency range so as to protect hearing. By means of the technical solution of using an internal microphone of the headset to pick up voice signals within the ear canal and environmental noise signals slipping into the ear canal, using an external microphone of the headset to pick up environmental noise signals and voice signals propagating through air, and obtaining transmitting terminal voice signals of the headset by eliminating the noise element in the signals picked up by the internal microphone and remaining the voice element with the signals picked up by the external microphone as reference signals, firstly, on an acoustic level, the signals within the ear canal picked up by the internal microphone have higher signal to noise ratio due to the function of the earplug and the external connection cavity; and secondly, on an electronic level, the clarity of the transmitting terminal signals is greatly improved and the voice is enhanced since the signals picked up by the internal and external microphones are self-adaptively filtered. Meanwhile, by means of the technical solution of using sound dynamic compression technology to cut down and compensate the signals picked up by the external microphone in terms of sound pressure level such that the sound pressure range is compressed to a range acceptable by human ears and the signals, the sound pressure of which has been compressed, and the voice signals received by the headset are broadcast together through a receiver of the headset, strong noises can be reduced to avoid damage to human's hearing, and the sound in a lower sound pressure level can be moderately increased such that the wearer can capture useful information therein so as to achieve monitoring the environment. As can be seen, the technical solution of the present invention can achieve protecting hearing, enhancing voice and monitoring three-dimensional environments under strong-noise environments.

DETAILED DESCRIPTION OF THE INVENTION

Figure 1:
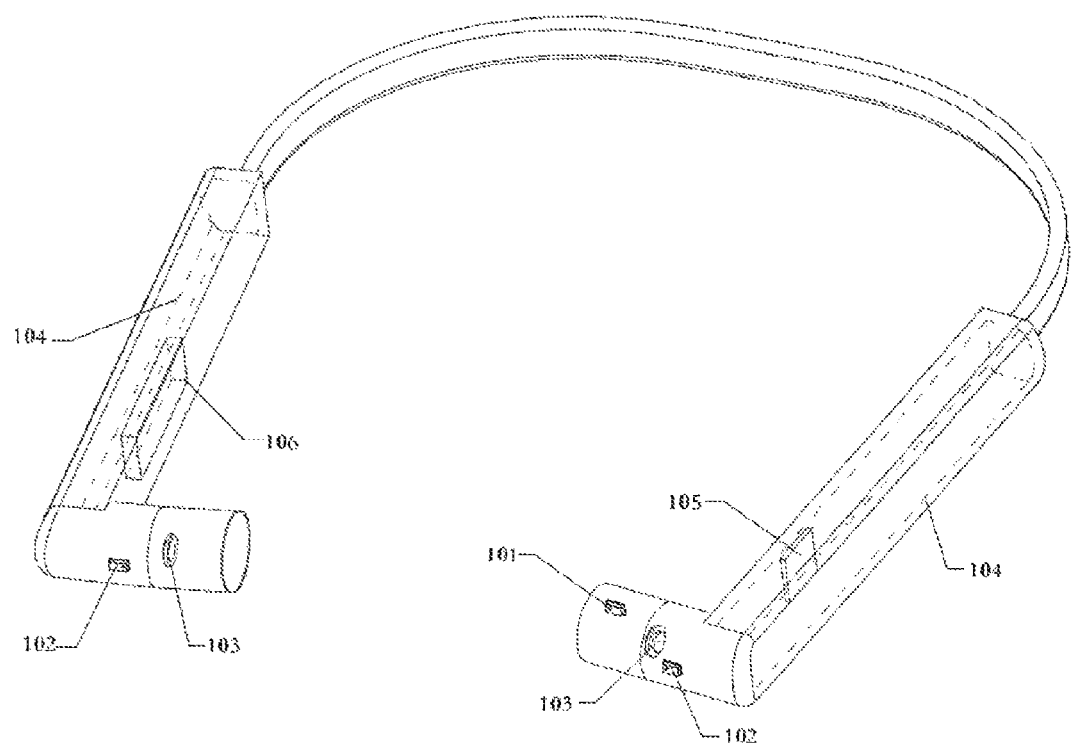
FIG. 1 is a structural diagram showing an embodiment of the invention when a headset communication method under a strong-noise environment is applied to a headset.

To make the object, technical solution and advantages of the present invention clearer, the embodiments of the present invention are described in further detail with reference to the drawings.

The headset communication method under a strong-noise environment in an embodiment of the invention comprises the following points:

(1) using an earplug closely coupled to the wearer's ear canal meatus to reduce medium and high frequency noises entering the ear canal, and using an external connection cavity extending from the earplug and constituting a parallel branch with the ear canal to divert medium and low frequency noises entering the ear canal, so as to eliminate noises from the sound signals entering the ear canal in a full frequency range.

Here, noise reduction in a full frequency range can be realized by means of combining passive noise reduction technology and sound diversion technology, which provides the process in (2) with voice signals having a higher signal to noise ratio.

(2) using an internal microphone of the headset to pick up voice signals within the ear canal and environmental noise signals slipping into the ear canal, and using an external microphone of the headset to pick up environmental noise signals and voice signals propagating through air; and obtaining transmitting terminal signals of the headset after eliminating the noise element in the signals picked up by the internal microphone and remaining the voice element with the signals picked up by the external microphone as reference signals.

Here, the voice is enhanced both acoustically (in earplug, external connection cavity and internal microphone) and electronically (self-adaptively filtering the signals of the internal and external microphones), thereby obtaining transmitting terminal signals having high clarity and naturalness.

(3) using a sound dynamic compression unit for using sound dynamic compression technology to cut down and compensate the signals picked up by the external microphone of the headset in terms of sound pressure level such that the sound pressure range of the processed signals (i.e., the signals cut down and compensated in terms of sound pressure level) is compressed to a range acceptable by human ears, and the processed signals and the receiving terminal signals received by the headset together are broadcast through a receiver of the headset.

Here, by means of sound dynamic compression technology, the intensity range of environmental noises is projected to the hearing domain of human ears, which not only avoids the possible damage to human ears by an instantaneous ultimate sound but also completely presents the background noises to the wearer's ears.

As can be seen, by effectively combining the technology of noise diversion, in-ear microphone and acoustic signal processing with the sound dynamic compression technology, the above method can achieve protecting hearing, enhancing voice and monitoring a three-dimensional environment under strong-noise environments.

FIG. 1 is a structural diagram showing an embodiment of the invention when a headset communication method under a strong-noise environment is applied to a headset. As shown in FIG. 1, the headset comprises:

an internal microphone 101 for picking up voice signals with higher signal to noise ratio within the ear canal to ensure the communication clarity;

binaural external microphones 102, by which monitoring a three-dimensional environment can be achieved, and three-dimensional realistic sound field can be reproduced; in addition, the external microphone 102 located at the same ear side as the internal microphone 101 also provides an environmental noise reference for voice enhancement;

binaural receivers 103 for broadcasting the environmental noise reference signals and the receiving terminal signals together;

binaural external connection cavities 104 (shown by dashed lines in the drawing) for achieving sound diversion to ensure noise isolation in a full frequency range so as to protect hearing;

a low-power DSP chip 105 for providing voice enhancement processing on an electronic level and sound dynamic compression processing; and a dry battery 106 for providing power to the DSP chip 105.

In order to describe the technical solution of the invention in more detail, a multi-functional headset having hearing protecting function, voice communication function and three-dimensional environment monitoring function under a strong-noise environment is described in below. Specifically, these three aspects are described separately.

1. Protecting Hearing

Figure 2:
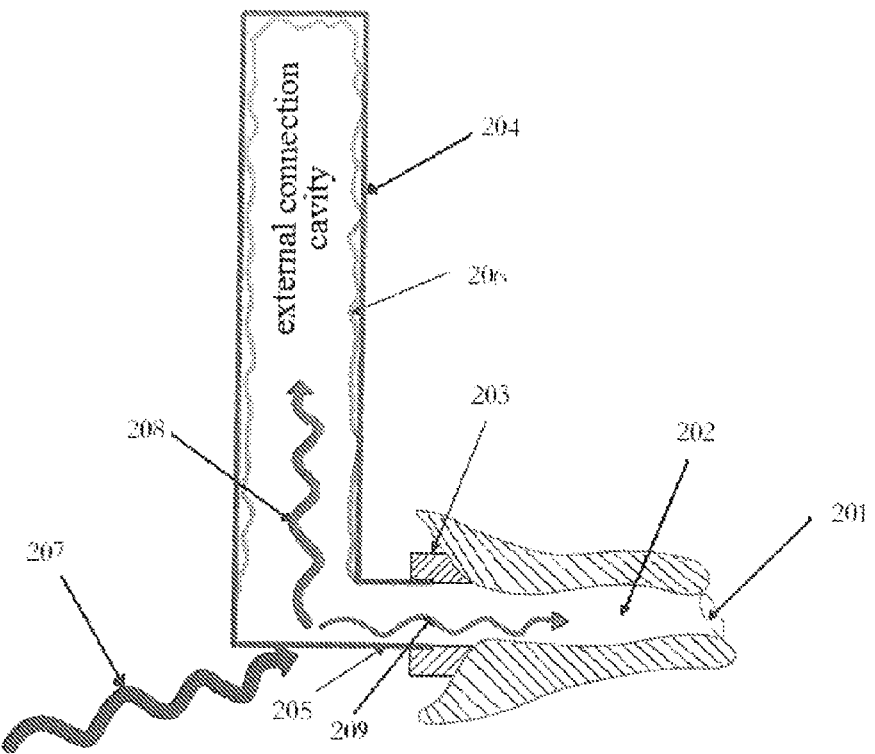
FIG. 2 is a structural diagram showing the sound diversion of a headset in an embodiment of the invention.

FIG. 2 is a structural diagram showing the sound diversion of a headset in an embodiment of the invention. FIG. 2 shows the structure of human ears, comprising an ear canal 202 and an eardrum 201. FIG. 2 also shows a diversion structure of the headset in an embodiment of the invention, comprising: an earplug 203 closely coupled to the wearer's ear canal meatus and having a perforation, and an external connection cavity 204 extending from the perforation of the earplug 203 and constituting a parallel branch with the wearer's ear canal. The external connection cavity 204 is connected to the perforation of the earplug 203 via a connection tube 205. A sound absorbing material is attached to the inner wall of the external connection cavity 204. The acoustic impedance of the external connection cavity 204 is significantly smaller than the acoustic impedance of the ear canal. Environmental noise 207 is diverted at the ear canal meatus. Since the acoustic impedance of the external connection cavity 204 is significantly smaller than the acoustic impedance of the ear canal, major noise 208 is diverted to the external connection cavity 204 and minor noise 209 enters the ear canal. The earplug 203 can reduce medium and high frequency noises entering the ear canal and the external connection cavity 204 can divert most of medium and low frequency noises, so noises can be reduced in a full frequency range.

Figure 3:
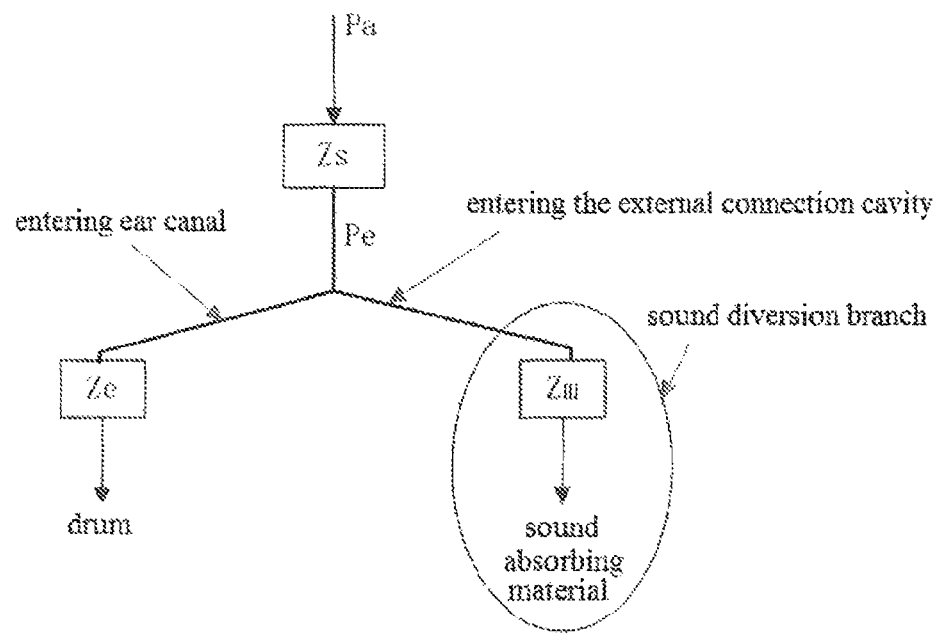
FIG. 3 is a principle diagram showing the sound diversion of a headset in an embodiment of the invention.

FIG. 3 is a principle diagram showing the sound diversion of a headset in an embodiment of the invention. Referring to FIG. 3, a tube or a cavity is closely coupled to the ear canal meatus. Seeing from the ear canal meatus, it is equivalent to that a parallel branch is added to the ear canal. The noises slipped to the entrance of the ear canal will be partially diverted by this branch. The smaller the acoustic impedance Zm of the branch is than the acoustic impedance Ze of the ear canal, the more acoustic energy enters the additional tube or cavity, thereby reducing the noises entering the ear canal.

Referring to FIG. 3, outside noises Pa firstly penetrates the equivalent acoustic impedance Zs of the headset and then reaches ear canal meatus. The sound pressure of the residual noises is Pe at the ear canal meatus. If there is no diversion branch, the residual noises whose sound pressure is Pe at the ear canal meatus will all enter the ear canal, penetrate the acoustic impedance Ze of the ear canal and finally reach the eardrum to arouse hearing, which is a passive noise reduction process. When a diversion branch is introduced, the residual noises whose sound pressure is Pe will be partially diverted by the diversion branch, and the sound pressure entering the ear canal will become as $$P'_e = \frac{Z_m}{Z_m + Z_e} P_e,$$

where $P'_e$ is the sound pressure of the residual noises entering the ear canal; when $Z_m$ is much smaller than $Z_e$, $$P'_e \approx \frac{Z_m}{Z_e} P_e.$$

As can be seen, the effect of sound diversion is directly determined by the ratio of $Z_m$ to $Z_e$. The smaller the ratio, the greater the diversion effect. The diverted tube or cavity exists primarily as a capacitive element, the impedance of which is $$Z_m \approx \frac{1}{j\omega C_a} = \frac{\rho_0 c_0^2}{j\omega V_a},$$

where $C_a$ is the acoustic volume of the additional cavity, $V_a$ is its volume, $c_0$ is the speed of sound in air, $\omega$ is the angular frequency, $\rho_0$ is the density of air. As can be seen, the greater the volume of additional cavity, the smaller its acoustic impedance, and the more obvious the diversion effect.

In an embodiment of the present invention, noises of 30 dB or more can be reduced in a full frequency range by means of combining passive noise reduction technology and sound diversion technology. Referring to FIG. 2, the structure in this part is constituted by an earplug 203 closely coupled to the ear canal meatus and an external connection cavity 204 extending from the earplug 203. The earplug 203 formed by a rubber or other acoustically resistive elastic materials can effectively block medium and high frequency noises. When the residual noises reach the entrance of the ear canal 202, they will face a passage formed by connecting the ear canal 202 and the external connection cavity 204 in parallel. If the acoustic impedance of the external connection cavity 204 is designed to be much smaller than the acoustic impedance of the ear canal 202, the majority of the acoustic energy will swarm into the external connection cavity 204 and be absorbed by the sound absorbing material on the wall of the cavity body through repeatedly scattering. In this way, the acoustic energy entering the ear canal 202 is reduced, thereby achieving the effect of reducing noises in a full frequency range. In addition, the linear degree of the external connection cavity 204 can be quantitatively controlled to produce resonance at a particular frequency such that a stronger sound elimination effect is produced in the vicinity of this frequency. By designing and controlling the internal acoustic structure of the external connection cavity and the distribution of the sound absorbing material attached to the inner cavity, the intensity and the frequency range of sound elimination by resonance can be adjusted so as to achieve the best noise reduction effect in a full frequency range.

2. Enhancing Voice

The voice enhancement solution adopted in the embodiment of the present invention comprises two portions: the first part is to acoustically enhance voice and provide the electronic voice enhancement algorithm with a primary signal of a better signal to noise ratio and a noise reference signal highly related to the primary signal; and the second part is to use an advanced acoustic signal processing method to further perform voice enhancement and post-process to the signals to increase the signal to noise ratio of the voice and improve the intelligibility and comfort of the voice of the transmitting terminal. In the following, the method for enhancing voice will be described on acoustic and electronic aspects, respectively.

Studies show that a closed cavity will be formed if the human ear canal is isolated from outside air, and when the person is speaking, the air in the ear canal will generate synchronous vibration that contains stronger voice signals. Therefore, in the headset provided by the present invention, the microphone within the ear canal picks up voice signals within the ear and residual noise signals slipping therein, and the external microphone picks up environmental noise signals. The signals of both the internal and external microphones are simultaneously sent to a voice signal processing unit; the signals of the internal microphone are as primary signals and the signals of the external microphone are as reference signals to self-adaptively eliminate the noise signals in the signals of the internal microphone on an electronic level by the self-adaptively filtering method and remain voice element; and finally, the self-adaptively filtered voice signals are spectrum compensated, thereby obtaining transmitting terminal voice signals of high clarity and naturalness. Please refer to FIGS. 4 and 5 for detail.

Figure 4:
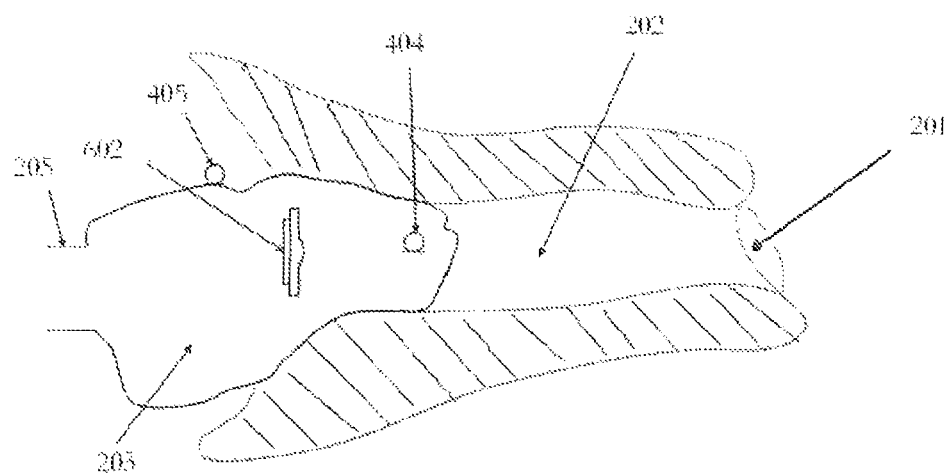
FIG. 4 is a structural diagram showing the in-ear portion of a headset in an embodiment of the invention.

FIG. 4 is a structural diagram showing the portion of the in-ear portion of a headset in an embodiment of the invention. FIG. 4 shows the structure of human ears, comprising an ear canal 202 and an eardrum 201. FIG. 4 also shows the structure of the in-ear portion of a headset in an embodiment of the invention, comprising: an earplug 203 closely coupled to the ear canal 202, an internal microphone 404 for picking up voice signals within the ear canal and residual noise signals slipping into the ear canal, and an external microphone 405 for picking up environmental noise signals. Referring to FIG. 4, the internal microphone 404 is located in the portion of the earplug 203 that can enter the ear canal when the headset is worn, and the external microphone 405 is located in the portion of the earplug 203 that is outside the ear canal when the headset is worn.

In addition, in the embodiment of the present invention, the headset further comprises: a voice signal processing unit for receiving the signals picked up by the internal microphone 404 and the signals picked up by the external microphone 405, and obtaining transmitting terminal signals of the headset after eliminating the noise element in the signals picked up by the internal microphone 404 and remaining the voice element with the signals picked up by the external microphone 405 as reference signals. The voice signal processing unit is not present in FIG. 4. The voice signal processing unit can be connected to the internal microphone 404 and the external microphone 405, respectively, and it can be positioned in a reasonable portion of the headset according to the actual condition, which does not affect the implementation of the embodiment of the present invention.

When a person is speaking, voice signals are delivered through the eustachian tube into the ear canal, and the muscle in the ear canal vibrates and generates air vibration when making sound, that is, voice is produced. When the ear canal meatus is open, the gas vibration (source) in the ear canal radiates toward a larger space (large load), so the gas vibrates with small amplitude and the acoustic energy is weak; when the ear canal meatus is blocked, the gas vibration (source) in the ear canal acts only in a very small space within the ear canal, so the gas vibrates with great amplitude, the acoustic energy is strong, the energy of the outside noises is reduced since they are passively and soundproofly transmitted into the ear canal, thereby greatly improving the signal to noise ratio. Thus, referring to FIG. 4, the internal microphone 404 picks up voice signals within the ear canal and environmental noise signals slipping into the ear canal, and the external microphone 405 picks up environmental noise signals and voice signals propagating through air. After passing through the obstruction of the earplug and the diversion of the external connection cavity, the environmental noises have been greatly attenuated when they enter the ear canal, so the voice signals picked up by the internal microphone 404 have had a higher signal to noise ratio. The purer outside noise signals picked up by the external microphone 405 can provide the noise reduction on an electronic level in the next step with better outside noise reference signals. Spatially, the distance between the internal microphone 404 and the external microphone 405 is relatively short, which ensures that the outside noise signals picked up have better relativity, thereby ensuring that the noise signals can be further reduced on an electronic level.

After enhancing voice on an acoustic level, the signal to noise ratio of the voice signals is further improved using acoustic signal processing technology on an electronic level and the naturalness and clarity of the voice signal are improved. See FIG. 5 for detail.

Figure 5:
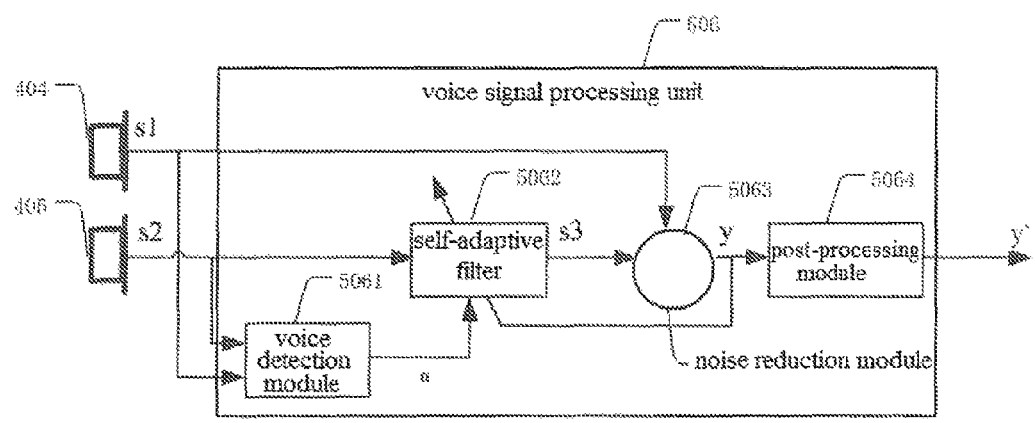
FIG. 5 is a structural block diagram showing the voice enhancement processing portion of headset in an embodiment of the invention.

FIG. 5 is a structural block diagram showing the voice enhancement processing portion of a headset in an embodiment of the invention. As shown in FIG. 5, the headset comprises: an internal microphone 404, an external microphone 405 and a voice signal processing unit 506. The voice signal processing unit 506 specifically comprises:

a voice detection module 5061 for receiving the signals s1 picked up by the internal microphone 404 and the signals s2 picked up by the external microphone 405, determining a control parameter α according to the statistical energy ratio of s2 to s1 in a low frequency range, and outputting the control parameter α;

a self-adaptive filter 5062 for updating the reference signals with the feedback output signals y as the weight, updating the control parameter of the speed with the control parameter α output by the voice detection module 5061 as the weight, self-adaptively filtering the received signals s2 of the external microphone 405, and outputting the self-adaptive filter output signals s3;

a noise reduction module 5063 for obtaining output signals y by subtracting the received self-adaptive filter output signals s3 from the received signals s1 picked up by the internal microphone 404;

and a post-processing module 5064 for single-channel voice processing and spectrum spreading processing the output signals y. The signal output by the post-processing module is transmitting terminal signals of the headset.

Voice detection module 5061: when there are voice signals, the internal microphone 404 picks up more voice signals within the ear canal; when the headset wearer is speaking loudly, the voice signals propagating through air and picked up by the external microphone 405 cannot be ignored. If the self-adaptive filter is updated directly using the signals of the external microphone 405 as reference signals, the voice may probably be damaged. Therefore, a voice detection module 5061 is added into the present invention to output control parameter α by it. The control parameter α is mainly used for weighting the convergence step size of the self-adaptive filter. The value of the control parameter α is mainly determined by calculating the statistical energy ratio of the external microphone to the internal microphone in a low frequency range, and the numerical range of α is $0 \leq \alpha \leq 1$.

Self-adaptive filter 5062 and noise reduction module 5063: the self-adaptive filter 5062 is a FIR filter with the step P ($P \geq 1$). The weight of the filter is $\overline{w}=[w(0), w(1), \ldots, w(P-1)]$. In an embodiment of the present invention, P=64. The input signals of the self-adaptive filter 5062 are $s2(n)$, where n is the discrete time number. The output signals of the self-adaptive filter are $s3(n)$. The offset signals y(n) is obtained by subtracting $s3(n)$ from $s1(n)$. y(n) is fed back to the self-adaptive filter to update the weight of the filter, and its updating speed is controlled by parameter α. When α=1, namely, all of $s1(n)$ and $s2(n)$ are noise element, the self-adaptive filter 5062 quickly converges to a transfer function H_noise by which noises are transmitted from the external microphone 405 to the internal microphone 404, to make $s3(n)$ the same as $s1(n)$, so the offset y (n) is very small, thereby eliminating the noises. When α=0, namely, all of $s1(n)$ and $s2(n)$ are target voice signals, the self-adaptive filter 5062 stops updating, so the self-adaptive filter 5062 will not converge to a transfer function H_speech by which voices are transmitted from the external microphone 405 to the internal microphone 404. $s3(n)$ is different from $s1(n)$, so the subtracted voice element will not be offset; y (n) is output while voice element is remained. When $0<\alpha<1$, namely, the signals collected by the microphone contains both voice element and noise element, the updating speed of the self-adaptive filter 5062 is controlled by the amount of voice element and noise element to ensure that voice element is remained while eliminating noises. Since the transfer function H_noise by which noises are transmitted from the external microphone 405 to the internal microphone 404 and the transfer function H_speech by which voices are transmitted from the external microphone 405 to the internal microphone 404 are similar, the voice will still be damaged to a certain degree even if the self-adaptive filter 5062 converges to H_noise. Therefore, α is used to restrict the weight of the self-adaptive filter 5062. In this embodiment, the restriction done is $\alpha*\overline{w}$ When α=1, namely, all of the signals collected are noise element, the self-adaptive filter 5062 is not restricted, and the noises are fully eliminated; when α=0, namely, all of the signals collected are voice element, the self-adaptive filter 5062 is entirely restricted, and the voices are fully remained; and when $0<\alpha<1$, namely, the signals collected by the microphone contain both voice element and noise element, the self-adaptive filter 5062 is partially restricted, and the noise portion is eliminated and the voices are completely remained. Thus, the effect of well protecting voices is achieved while reducing noises.

Post-processing module 5064: the post-processing module 5064 comprises two portions: firstly, single-channel voice enhancement processing the signals output by the noise reduction module 5063 to further increase the signal to noise ratio of the voice signals, and then spectrum spreading the single-channel processed signals to improve the clarity and intelligibility of the output voice signals. Single-channel voice enhancement and spectrum spreading can be carried out by the existing mature solution, and they will not be mentioned here in detail.

From the above, it can be seen that by means of the headset in the embodiment of the present invention, on the aspect of voice enhancement, an internal microphone picks up voice signals within the ear canal to obtain the voice signals with higher signal to noise ratio, achieving the voice enhancement on an acoustic level; an external microphone picks up environmental noises to provide conditions to the voice enhancement on an electronic level; and on the electronic level, background noises are further eliminated by self-adaptively filtering means based on the signals of the internal microphone with the help of the signals of the external microphone. Comparing with the existing method for voice enhancement using a close-talking microphone, this solution can still provide, even under an ultimate noisy condition, original signals with a sufficient signal to noise ratio as a basis for the detection and determination of voice signals, thereby ensuring the clarity and intelligibility of the transmitting terminal voice.

It should be noted that, in this embodiment, sound diversion technology is used and most of the noises reaching the ear canal meatus are diverted using an external connection cavity, thus, environmental noises have been greatly attenuated after they have passed through the earplug and experienced sound diversion, and the voice signals picked up by the internal microphone 404 have had a higher signal to noise ratio.

3. Monitoring a Three-Dimensional Environment

Figure 6:
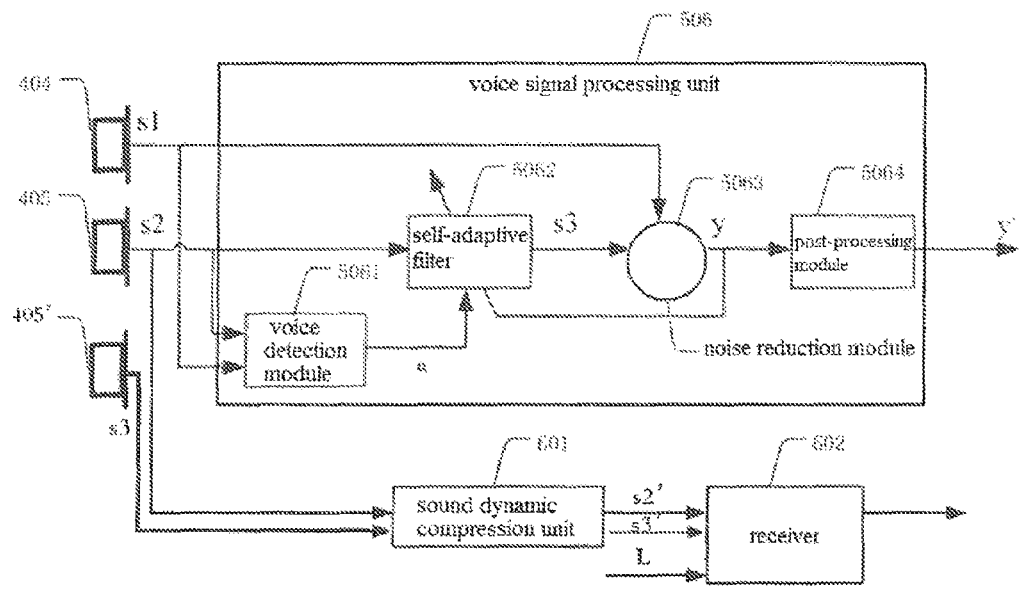
FIG. 6 is a structural block diagram showing the headset of FIG. 5 to which the function of monitoring three-dimensional environments is further added.

FIG. 6 is a structural block diagram showing the headset of FIG. 5 to which the function of monitoring three-dimensional environments is further added. Referring to FIG. 6 and FIG. 4, the headset in this embodiment comprises the structure of the headset shown in FIG. 5, based on which, the headset in this embodiment further comprises:

An external microphone 405' on the other ear side; wherein the external microphone 405 and the external microphone 405' are located on the two ear sides respectively, and the external microphone 405 and the internal microphone 404 are located on the same ear side;

a sound dynamic compression unit 601 for receiving the signals s2 picked up by the external microphone 405 and the signals s3 picked up by the external microphone 405', and compressing the overall sound pressure range of the signals s2 and s3 picked up by the two external microphones to a range acceptable by human ears using sound dynamic compression technology;

and a receiver 602 for broadcasting within the wearer's ear the signals s2' and s3' processed by the sound dynamic compression unit 601 together with the transmitting terminal signals L received by the headset.

In this embodiment, the number of the internal microphone is 1, which is located on the left or right ear side; the number of the external microphone is 2, which are located on the left and right ear sides, respectively. The voice signal processing unit receives the signals picked up by the internal microphone and the external microphone that are located at the same ear side. The sound dynamic compression unit cuts down and compensates the signals picked up by the two external microphones in terms of sound pressure level.

In the embodiment of the present invention, in terms of monitoring a three-dimensional environment, environmental noises are picked up by the external microphone 405 and the external microphone 405' and transmitted into the sound dynamic compression unit 601. In the sound dynamic compression unit 601, the quantity of energy of the signals is firstly estimated in the time domain or frequency domain to adjust the gain according to the quantity of the energy. To be specific, a small gain (less than 1) is given to the signals having high energy, and a large gain (greater than 1) is given to the signals having low energy. Upon such adjustment, strong noises in the environment that are harmful to human hearing are reduced, and the sounds on lower sound pressure levels are increased appropriately such that the wearer can capture the useful information therein. Under the condition of not damaging environmental sound information, the overall sound pressure dynamic range is compressed into a range acceptable by human ears. For example, the sound pressure range of the environmental noises is 20 dB-160 dB, and it can be compressed to a range of 40 dB-90 dB after processing.

As can be seen, in this embodiment, by cutting down and compensating the signals picked up by the external microphones on both sides of the headset in terms of sound pressure level, the sound pressure range thereof is compressed to a range adapted to be received by human ears, and the processed signals and the receiving terminal signals received by the headset are broadcast together through the receiver of the headset.

Figure 7:
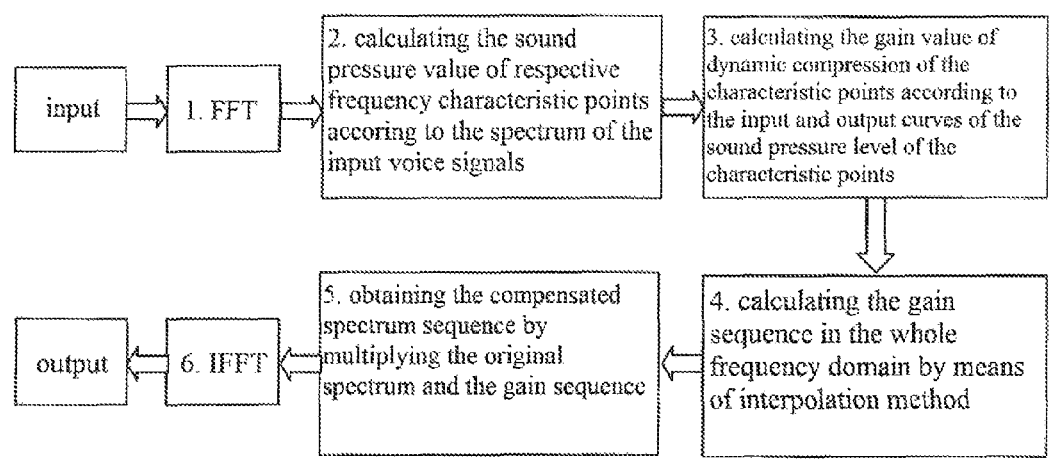
FIG. 7 is a flowchart showing the sound dynamic compression algorithm in an embodiment of the invention.
Figure 8:
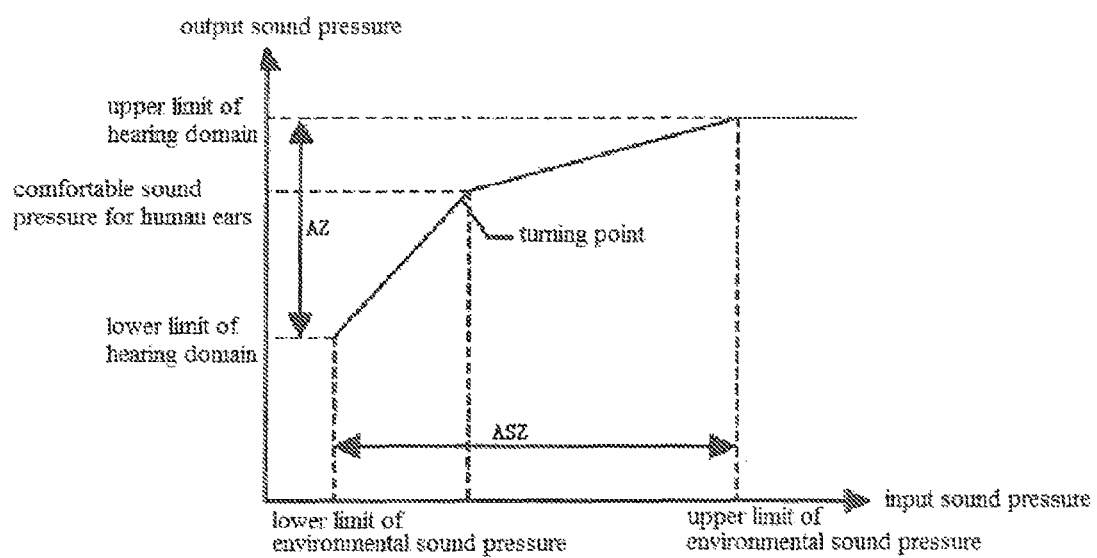
FIG. 8 is a curve showing the sound dynamic compression effect in an embodiment of the invention.

FIG. 7 is a flowchart showing the sound dynamic compression algorithm in an embodiment of the invention. FIG. 8 is a curve showing the sound dynamic compression effect in an embodiment of the invention. Referring to FIGS. 7 and 8, in terms of monitoring a three-dimensional environment, environmental sounds are picked up by the external microphone 405 and transmitted into the sound dynamic compression unit 601. The processing procedure in the sound dynamic compression unit 601 is as shown in FIG. 7, mainly comprising the following sections: 1. Fourier transforming; 2. calculating the sound pressure of the characteristic points; 3. determining the gain value of the characteristic points; 4. calculating the gain sequence in the whole frequency domain by calculating the difference; 5. obtaining a spectrum after compensated; and 6. inverse Fourier transforming. The processed result is to project an ambient sound zone (ASZ) to an audibility zone (AZ), see FIG. 8. The signals processed by the sound dynamic compression unit 601 and the voice signals received by the headset are broadcast together by the receiver 602 within the wearer's ear, which will not damage the wearer's hearing, and meanwhile allow the wearer to monitor the sounds in the surrounding environment.

In the embodiment of the present invention, the voice signal processing unit 506 and the sound dynamic compression unit 601 are integrated into a DSP chip. The headset in the embodiment of the present invention further comprises a dry battery for providing power to the DSP chip. The power consumption of DSP chip supplied by the dry battery is very low, guaranteeing a strong endurance.

To sum up, by efficiently combining noise diversion technology, in-ear microphone technology and sound dynamic compression technology, the embodiment of the present invention provides a multifunctional headset that can provide effective hearing protection, clear voice communication function and three-dimensional environment monitoring. By comparing the existing headset, the headset in the embodiment has following advantages:

(1) In the aspect of protecting hearing, noises of 30 dB or more can be reduced in a full frequency range by means of particular sound diversion technology; in addition, since the passive noise reduction technology is used and the active noise reduction technology that has complicated structure and high energy consumption is abandoned, the electric power of the headset is reduced, greatly increasing the endurance of the headset.

(2) In the aspect of voice communication, comparing with the existing method for voice enhancement using a close-talking microphone or a bone-conducting microphone, this method, by means of picking up voice signals within ear by an in-ear microphone and further eliminating background noises by a voice signal processing unit, can still provide, even under an ultimate noisy condition, original signals with a sufficient signal to noise ratio for the detection and determination of voice signals.

(3) In the aspect of monitoring environment, by means of sound dynamic compression technology, the intensity range of environmental noises is projected to the hearing domain of human ears through advanced sound dynamic compression algorithm, which not only avoids the possible damage to human ears by an instantaneous ultimate sound pressure but also presents the entire background noises to the wearer's ears.

The foregoing is only a preferred embodiment of the present invention, and it is not used for limiting the protection scope of the present invention. Any modification, equivalent replacement and improvement within the spirit and principles of the present invention should be included in the protection scope of the present invention.

The invention claimed is:

1. A headset communication method under a strong-noise environment, wherein the method comprises:
   using an earplug closely coupled to the wearer's ear canal meatus to reduce medium and high frequency noises entering the ear canal, and using an external connection cavity extending from the earplug and constituting a parallel branch with the ear canal to divert medium and low frequency noises entering the ear canal, so as to reduce noises from the sound signals entering the ear canal in a full frequency range;
   using an internal microphone of the headset to pick up voice signals within the ear canal and environmental noise signals slipping into the ear canal, and using an external microphone of the headset to pick up environmental noise signals and voice signals propagating through air; and obtaining transmitting terminal signals of the headset after eliminating the noise element in the signals picked up by the internal microphone and remaining the voice element with the signals picked up by the external microphone as reference signals;
   cutting down and compensating the signals picked up by the external microphones at both sides of the headset in terms of sound pressure level such that the sound pressure range of the processed signals is compressed to a range acceptable by human ears and the processed signals and the receiving terminal signals received by the headset are broadcast together through a receiver of the headset.

2. According to the method of claim 1, wherein
   the acoustic impedance of the external connection cavity is significantly smaller than the acoustic impedance of the ear canal; and a sound absorbing material is attached to the inner wall of the external connection cavity.

3. According to the method of claim 1, wherein the step of obtaining transmitting terminal signals of the headset after eliminating the noise element in the signals picked up by the internal microphone and remaining the voice element with the signals picked up by the external microphone as reference signals, comprises:
   determining a control parameter $\alpha$ according to the statistical energy ratio of the signals picked up by the external microphone to the signals picked up by the internal microphone in a low frequency range; and updating the weight of the self-adaptive filter with the feedback output signals, controlling the updating speed of the weight of the self-adaptive filter with the control parameter $\alpha$, and self-adaptively filtering the signals picked up by the external microphone, to obtain self-adaptive filter output signals;
   obtaining output signals by subtracting the self-adaptive filter output signals from the signals picked up by the internal microphone; and
   using the output signals as transmitting terminal signals of the headset.

4. According to the method of claim 3, wherein the method further comprises: single-channel voice processing and spectrum spreading processing the output signals; and
   using the single-channel voice processed and spectrum spreading processed signals as transmitting terminal signals of the headset.

5. A headset, wherein the headset comprises:
   an earplug closely coupled to the wearer's ear canal meatus to reduce medium and high frequency noises entering the ear canal; an external connection cavity extending from the earplug and constituting a parallel branch with the ear canal to divert medium and low frequency noises entering the ear canal;
   an internal microphone for picking up voice signals within the ear canal and environmental noise signals slipping into the ear canal; an external microphone for picking up environmental noise signals and voice signals propagating through air; a voice signal processing unit for receiving the signals picked up by the internal microphone and the signals picked up by the external microphone and obtaining transmitting terminal signals of the headset after eliminating the noise element in the signals picked up by the internal microphone and remaining the voice element with the signals picked up by the external microphone as reference signals;
   a sound dynamic compression unit for using sound dynamic compression technology to cut down and compensate the signals picked up by the external microphone in terms of sound pressure level such that the sound pressure range of the processed signals is compressed to a range acceptable by human ears; and
   a receiver for broadcasting the signals processed by the sound dynamic compression unit and the receiving terminal signals received by the headset together.

6. According to the headset of claim 5, wherein
   the acoustic impedance of the external connection cavity is significantly smaller than the acoustic impedance of the ear canal; and
   a sound absorbing material is attached to the inner wall of the external connection cavity.

7. According to the headset of claim 5, wherein, the voice signal processing unit comprises:
   a voice detection module for receiving the signals picked up by the internal microphone and the signals picked up by the external microphone, determining a control parameter $\alpha$ according to the statistical energy ratio of the signals picked up by the external microphone to the signals picked up by the internal microphone in a low frequency range, and outputting the control parameter $\alpha$;
   a self-adaptive filter for updating the reference signals with the feedback output signals as the weight, updating the control parameter of the speed with the control parameter $\alpha$ as the weight, self-adaptively filtering the received signals of the external microphone, and outputting the self-adaptive filter output signals;
   and, a noise reduction module for obtaining output signals by subtracting the received self-adaptive filter output signals from the received signals picked up by the internal microphone.

8. According to the headset of claim 7, wherein, the voice signal processing unit further comprises:
   a post-processing module for single-channel voice processing and spectrum spreading processing the output signals.

9. According to the headset of claim 5, wherein, the voice signal processing unit and the sound dynamic compression unit are integrated into a DSP chip.

10. According to the headset of claim 5, wherein
    the number of the internal microphone is 1, which is located on the left or right ear side of the headset;

the number of the external microphone is 2, which are located on the left and right ear sides of the headset, respectively;

the voice signal processing unit receives the signals picked up by the internal microphone and the external microphone that are located at the same ear side; and the sound dynamic compression unit cuts down and compensates the signals picked up by the two external microphones in terms of sound pressure level.

* * * * *